(12) United States Patent
Fan et al.

(10) Patent No.: US 11,205,336 B2
(45) Date of Patent: Dec. 21, 2021

(54) SEAT

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Litao Fan, Beijing (CN); Hongyang Yu, Beijing (CN)

(73) Assignees: Beijing BOE Optoelectronics Technology Co., Ltd., Beijing (CN); BOE Technology Group Co., Ltd., Beijing (CN)

( * ) Notice: Subject to any disclaimer, the term of this patent is extended or adjusted under 35 U.S.C. 154(b) by 228 days.

(21) Appl. No.: 16/507,670

(22) Filed: Jul. 10, 2019

(65) Prior Publication Data
US 2020/0211353 A1 Jul. 2, 2020

(30) Foreign Application Priority Data
Jan. 2, 2019 (CN) .......................... 201920003308.X

(51) Int. Cl.
G08B 21/04 (2006.01)
A47C 7/72 (2006.01)
H04R 1/02 (2006.01)

(52) U.S. Cl.
CPC .......... *G08B 21/0461* (2013.01); *A47C 7/727* (2018.08); *H04R 1/025* (2013.01)

(58) Field of Classification Search
CPC ............................ G08B 21/0461; A47C 7/727
See application file for complete search history.

(56) References Cited

U.S. PATENT DOCUMENTS

2014/0127658 A1* 5/2014 Rekimoto .............. G09B 19/00
434/247

FOREIGN PATENT DOCUMENTS

CN 102058264 A 5/2011

OTHER PUBLICATIONS

First Office Action for CN Appl. No. 201920003308.X, dated Aug. 21, 2019.

* cited by examiner

*Primary Examiner* — Curtis B Odom
(74) *Attorney, Agent, or Firm* — The Webb Law Firm

(57) ABSTRACT

The present disclosure relates to a seat, comprising: a seat base; a seat frame; and a sitting posture detection device configured to alert a user when a sitting posture of the user sitting on the seat deviates from a standard sitting posture, wherein the sitting posture detection device includes: one or more distance sensors configured to measure a distance from the seat frame to one or more body parts of the user; and a processor configured to determine, according to the distance detected by the distance sensor, whether the sitting posture of the user deviates from the standard sitting posture, and issue an alarm information if the sitting posture of the user deviates from the standard sitting posture.

13 Claims, 7 Drawing Sheets

SEAT

CROSS-REFERENCE TO RELATED APPLICATIONS

The present application claims priority to Chinese Patent Application No. 201920003308.X, filed on Jan. 2, 2019, the disclosure of which is hereby incorporated by reference in its entirety.

TECHNICAL FIELD

The present disclosure relates to a seat.

BACKGROUND

For children or adults sitting to study or read, there are certain requirements for sitting posture when reading and writing. The key to maintaining eyesight is correct sitting posture. Once a bad sitting habit is developed, it will affect not only the eyes, but also other parts of the body (neck, chest, waist, etc.).

SUMMARY

According to an aspect of the present disclosure, there is provided a seat, comprising: a seat base; a seat frame; and a sitting posture detection device configured to alert a user when a sitting posture of the user sitting on the seat deviates from a standard sitting posture, wherein the sitting posture detection device includes: one or more distance sensors configured to measure a distance from the seat frame to one or more body parts of the user; and a processor configured to determine, according to the distance detected by the distance sensor, whether the sitting posture of the user deviates from the standard sitting posture, and issue an alarm information if the sitting posture of the user deviates from the standard sitting posture.

According to some embodiments of the present disclosure, the body part comprises a neck, a left shoulder, a right shoulder and a waist.

According to some embodiments of the present disclosure, the distance sensors are infrared range sensors or laser sensors.

According to some embodiments of the present disclosure, the sitting posture detection device further comprises a first support portion and a second support portion, a position of the first support portion corresponds to a position of a neck of the user in the standard sitting posture, a position of the second support portion corresponds to a position of a shoulder of the user in the standard sitting posture, and the distance sensors are respectively disposed on the first support portion and the second support portion.

According to some embodiments of the present disclosure, the sitting posture detection device further comprises a carrier rod, the first support portion and the second support portion are mounted on the carrier rod, so that the distance sensors can be rotated about the carrier rod to adjust angles of the distance sensors and can be moved along the carrier rod.

According to some embodiments of the present disclosure, the sitting posture detection device further comprises a carrier rod support portion fixedly coupled to the seat frame, the carrier rod being configured to be slidable on the carrier rod support portion to adjust a height of the distance sensors.

According to some embodiments of the present disclosure, the processor is configured to compare the distance measured by the distance sensors to a standard distance which is measured by the distance sensors when the user is in the standard sitting posture.

According to some embodiments of the present disclosure, when a difference between the distance measured by the distance sensors and the standard distance is greater than a predetermined threshold, the processor issues the alarm information.

According to some embodiments of the present disclosure, the sitting posture detection device comprises an alarming device.

According to some embodiments of the present disclosure, the alarming device comprises a speaker and a vibrator.

According to some embodiments of the present disclosure, the sitting posture detection device comprises a storage device for storing the standard distance.

According to another aspect of the present disclosure, there is provided a method of detecting a sitting posture of a user sitting on a seat, comprising: measuring a distance from a seat frame to one or more body parts of the user; determining whether the sitting posture of the user deviates from a standard sitting posture according to the distance; and issuing alarm information if the sitting posture of the user deviates from the standard sitting posture.

According to some embodiments of the present disclosure, the body part comprises a neck, a left shoulder, a right shoulder and a waist.

According to some embodiments of the present disclosure, the step of determining whether the sitting posture of the user deviates from a standard sitting posture according to the distance comprises: comparing the distance to a standard distance which is measured when the user is in the standard sitting posture; and if a difference between the distance and the standard distance is greater than a predetermined threshold, determining that the sitting posture of the user deviates from the standard sitting posture.

BRIEF DESCRIPTION OF THE DRAWINGS

The above and other objects, features and advantages of the present disclosure will be more readily understood by reference to the embodiments of the present disclosure in conjunction with the accompanying drawings. The components in the figures are only for the purpose of illustrating the principles of the present disclosure. In the figures, the same or similar technical features or components will be denoted by the same or similar reference signs.

DETAILED DESCRIPTION

Figure 1:
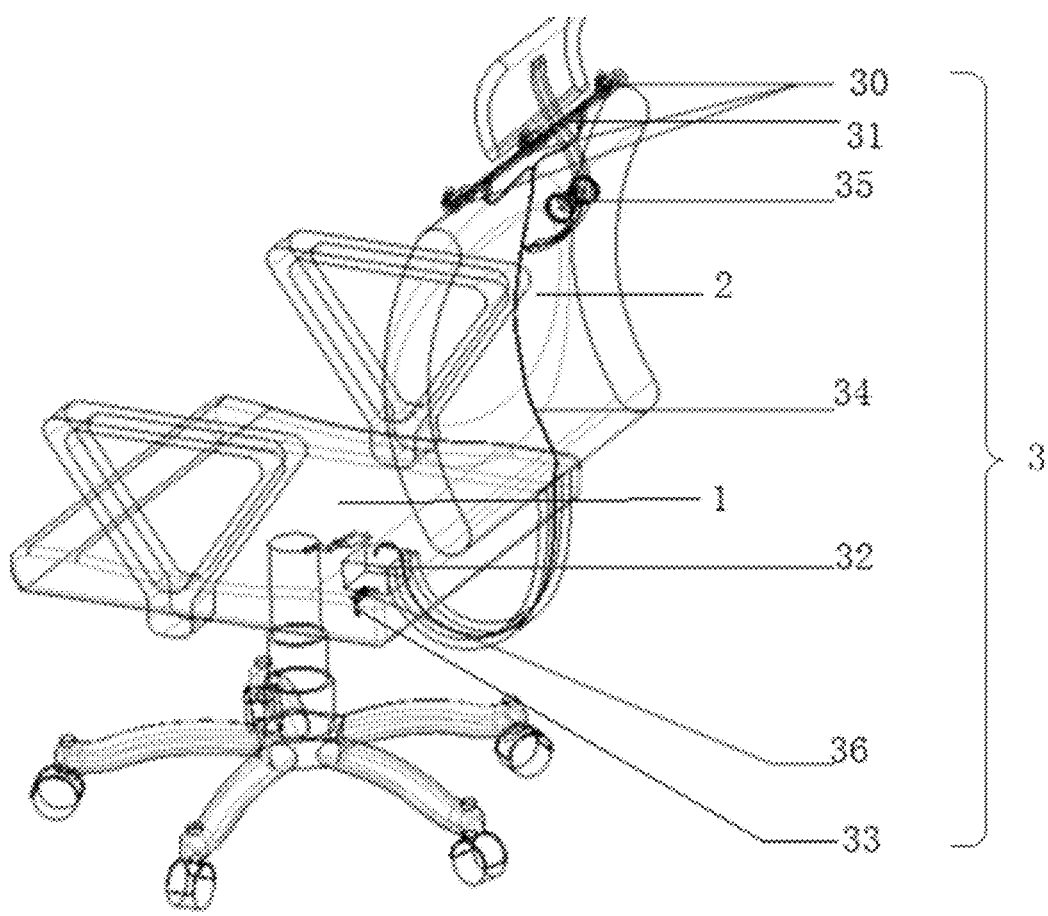
FIG. 1 shows a schematic structural view of a seat according to an embodiment of the present disclosure.

Below, embodiments of this disclosure will be described with reference to the drawings. The elements and features described in one of the figures or one embodiment of the present disclosure may be combined with elements and features illustrated in one or more other figures or embodiments. It should be noted that, for the sake of clarity, representations and descriptions of components and processes that are not known to those of ordinary skill in the art are omitted in the drawings and the description.

Figure 8:
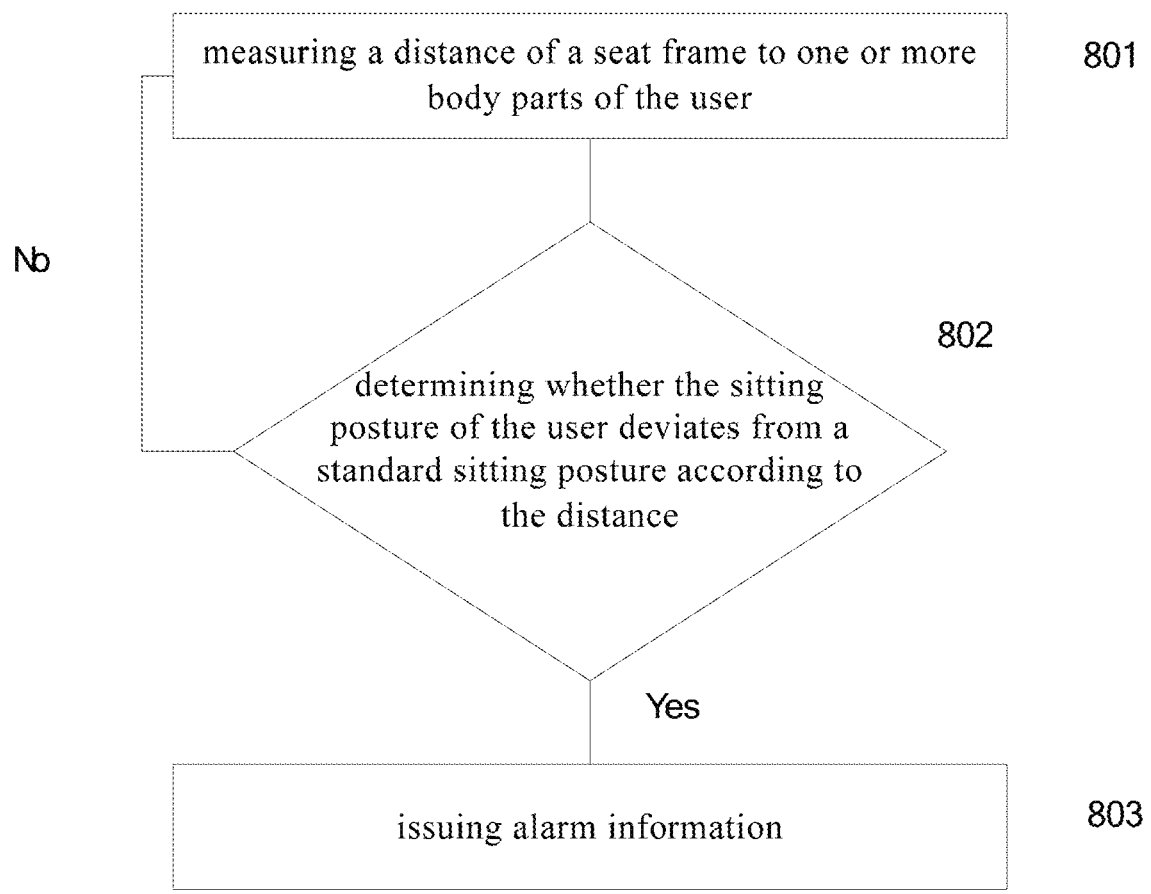
FIG. 8 is a flow chart of a method of detecting a sitting posture of a user sitting on a seat according to an embodiment of the present disclosure.

FIG. 8 is a flow chart of a method of detecting a sitting posture of a user sitting on a seat according to some embodiments of the present disclosure. As shown in FIG. 8, the method comprises:

measuring a distance of a seat frame to one or more body parts of the user (801);

determining whether the sitting posture of the user deviates from a standard sitting posture according to the distance (802); and in the case where the sitting posture of the user deviates from the standard sitting posture, issuing alarm information (803).

The structure of the seat and the method of detecting the sitting posture of a user sitting on the seat will be described in detail below in conjunction with the structural schematic diagram of the seat.

FIG. 1 shows a schematic structural view of a seat 100 according to an embodiment of the present disclosure. The main component modules of the seat 100 are as shown in FIG. 1 and comprise a seat base 1, a seat frame 2, and a sitting posture detection device 3. The sitting posture detection device 3 is fixedly mounted to the seat frame 2 and configured to measure a distance from the seat frame 2 to the user using a set of distance sensors 30, reminding the user to check his/her sitting posture. The sitting posture detection device 3 comprises: a set of distance sensors 30 for measuring sitting posture information of a user sitting on the seat, a mounting member 31 for fixing the sitting posture detection device to the seat, a central control system 32 mounted under the seat base 1, a charging line 33, a transmission line 34 for transmitting signals such as control signals, an alarming device 35 for warning the user of deviation from a standard position, and a power source 36, etc. In this embodiment, the seat detects whether a distance from the user sitting on the seat to the seat frame 2 meets a specified standard distance by using the distance sensors, so as to determine whether the sitting posture of the user is correct. Once a deviation from the specified standard distance is detected, the sitting posture detection device 3 will send a warning signal to remind the user sitting on the seat to adjust his/her sitting posture. The technical solution is smart and easy to implement, capable of facilitating the user of the seat to maintain a correct sitting posture.

Figure 2:
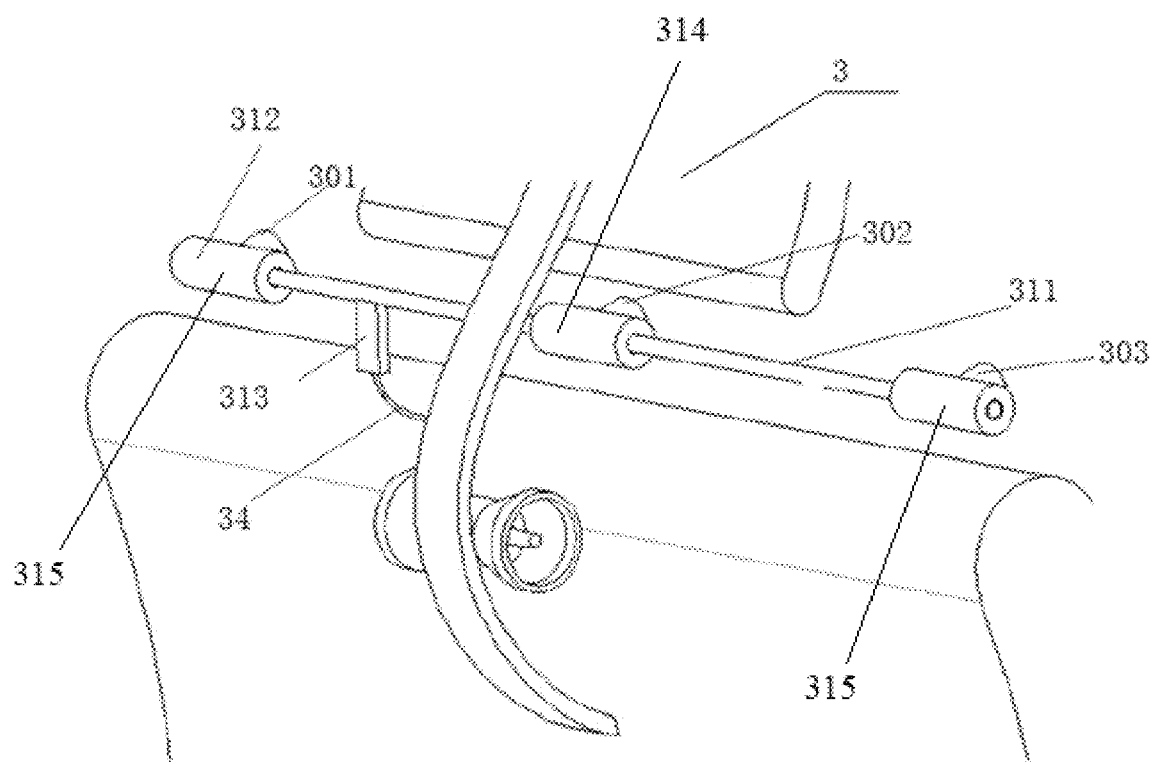
FIGS. 2 to 3 are schematic views showing a portion of the sitting posture detection device of FIG. 1.
Figure 3:
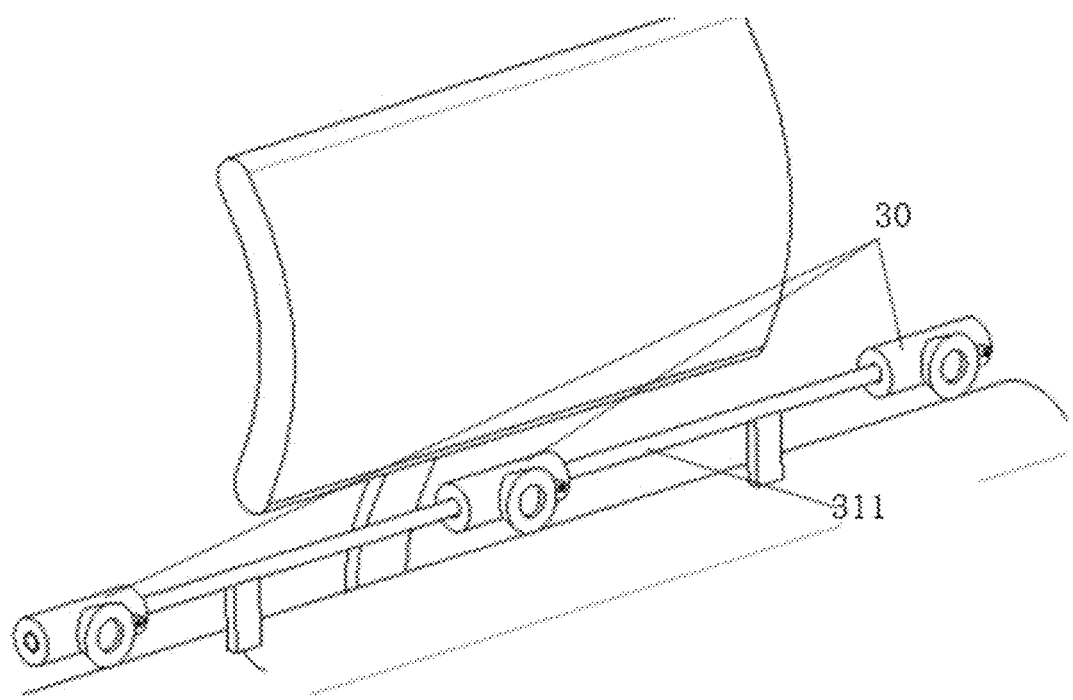

FIGS. 2 to 3 are schematic views showing a portion of the sitting posture detection device 3 of FIG. 1. The sitting posture detection device 3 comprises a set of distance sensors 30, a mounting member 31 and a signal transmission line 34. Wherein, the set of distance sensors 30 comprises one or more distance sensors 301, 302, 303. In order to facilitate installation and reduce the overall volume, each of the distance sensors may be an infrared range sensor. In addition, other types of distance sensors such as laser sensors can also be used. Alternatively, in the case where one distance sensor is used, its mounting position can be aligned with a central position of the user's neck. Alternatively, in the case where a plurality of distance sensors are used, they may be mounted on the sitting posture detection device 3 at a plurality of positions corresponding to a plurality of body parts of the user in a standard sitting posture. In the embodiment shown in FIG. 2 and FIG. 3, the distance sensors 301, 302, and 303 are three infrared range sensors, i.e., a distance sensor 302 corresponding to the neck, a distance sensor 301 corresponding to the left shoulder, and a distance sensor 303 corresponding to right shoulder. By sensing a plurality of parts of the user's body with a plurality of distance sensors, the sitting posture detection may be more precise.

According to an embodiment of the present disclosure, the mounting member 31 of the sitting posture detection device 3 comprises: a first support portion 314 arranged at a position corresponding to the neck of the user in a standard posture and used for mounting a distance sensor corresponding to the neck, and a second support portion 315 arranged at a position corresponding to the shoulder of the user in the standard posture and used for mounting a distance sensor corresponding to the left shoulder and a distance sensor corresponding to the right shoulder. The requirement of multi-point measurement can be sanctified by the arrangement of the first support portion 314 and the second support portion 315.

According to an embodiment of the present disclosure, the positions of the first support portion 314 and the second support portion 315 are adjustable in the horizontal direction or the height direction. The first support portion 314 and the second support portion 315 may be provided to be connected together, or may be provided separately.

In the case where the first support portion 314 and the second support portion 315 are provided separately, the first support portion 314 and the second support portion 315 may be provided in the form of separate mounting members, for example, separate magnets, electromagnets or screws for separate multi-point mounting. The first support portion 314 and the second support portion 315 are directly or indirectly mounted to the seat frame 2.

In the case where the first support portion 314 and the second support portion 315 are provided to be connected together, for example, as shown in FIG. 2 and FIG. 3, the following arrangement may be adopted, in which the sitting posture detection device is further provided with a carrier rod 311. On the carrier rod 311, there are the first support portion 314 and the second support portion 315 that are assembled to the rotation shaft of each distance sensor, and each distance sensor being fixed or integrally connected to the rotation shaft 312 of the distance sensor. Each of the distance sensors 301, 302, 303 is rotatable about the carrier rod 311 to adjust the angle of the distance sensors, and can be shifted and locked along the carrier rod 311. For example, each of the distance sensors 301, 302, 303 can be shifted along the carrier rod 311 to a certain position (such as, the positions corresponding to the left and right shoulders and neck of the user when the user is sitting on the seat in a standard posture) and then is secured (locked) at the position. With the carrier rod 311, the distance sensors can be flexibly shifted in the horizontal direction, and the pitch angle of each of the distance sensors can be flexibly adjusted.

The carrier rod 311 may be directly mounted to the seat frame, or the carrier rod 311 may be indirectly mounted to the seat frame via the carrier rod support portion 313.

As shown in FIGS. 2 and 3, the carrier rod 311 is mounted and supported by the carrier rod support portion 313, and the sitting posture detection device 3 is mounted to the seat frame 2. The carrier rod 311 can be slid up and down along the carrier rod support portion 313 and locked at a proper position. The height of the distance sensors 301, 302, 303 can locked by adjusting the sliding position of the carrier rod 311 on the carrier rod support portion 313. The carrier rod support portion 313 increases the flexibility of positioning of the distance sensors 301, 302, 303 in height. Preferably, the carrier rod support portion 313 is provided on the upper portion or the top portion of the seat frame 2, but is not limited thereto as long as it can secure the sitting posture detection device 3 and support the carrier rod 311.

According to some embodiments of the present disclosure, a distance sensor 304 corresponding to the waist of the user may be further provided on the sitting posture detection device 3, in order to measure a distance from the seat frame 2 to a position corresponding to the waist of the user. The addition of the measurement of the waist position allows for more accurate measurement and sitting posture detection.

In some embodiments according to the present disclosure, the sitting posture detection device 3 may measure a distance from the seat frame 2 to the user sitting on the seat base 1 in real time or periodically by using the distance sensors 301, 302, 303 and/or 304. Once there is a deviation from a standard distance (for example, a distance from the seat frame 2 to a respective body part of the user sitting on the seat base 1 in a standard sitting posture) exceeds a preset threshold, the sitting posture detection device 3 issues an alarm. This method of comparing the difference between the standard distance and the measured distance with a preset threshold is simple and reliable. Alternatively, a standard distance can be obtained by the user consciously maintaining the standard sitting posture, and can be stored in advance in a database, for example.

According to some embodiments of the present disclosure, the sitting posture detection device 3 includes an alarming device 35. The alarming device 35 may be a speaker for emitting a sound warning, such as a voice or music warning. Further, the alarming device 35 may also be, for example, a vibrator that can alert the user by generating vibration. In addition, multiple alarming devices can also be provided to facilitate the user to perform operations as needed.

The sitting posture detection device 3 further includes a storage device 601 for storing data of the standard distance from the seat frame 2 to the user in a standard sitting posture and the actual distance from the seat frame 2 to the user measured in real time or periodically. The storage device 601 records data such as the standard distance and the actual distance, which can be used for subsequent comparison, and can be used to analyze the user's sitting habit according to the statistical distance data, in order to provide a customized warning.

The detailed operation performed in the case where the carrier rod 311 and the carrier rod support portion 313 are provided will be described below. In FIG. 2 to FIG. 3, three infrared range sensors are mounted at different positions of the horizontally arranged carrier rod 311, and the position of the distance sensor 301 corresponding to the neck on the carrier rod 311 can be higher than the position of the distance sensor 302 corresponding to the left shoulder and the position of the distance sensor 303 corresponding to the right shoulder. The three infrared range sensors 301, 302, 303 can be independently rotated around the carrier rod 311, that is, the carrying rod 311 may serve as a horizontal pivot of the infrared range sensors 301, 302, 303. The angle such as the pitch angle at which each of the infrared range sensors 301, 302, 303 transmits or receives signals is adjusted through rotation around the pivot, enabling the rays emitted from the infrared range sensors 301, 302, 303 at a same height with the center of the neck in the height direction. The three infrared range sensors 301, 302, 303 are slidable along the carrier bar 311 and locked at appropriate positions in the horizontal direction. The height of the three infrared range sensors 301, 302, 303 can be locked by adjusting the up and down sliding position of the carrier bar 311 on the carrier rod support portion 313.

After sitting on the seat, the user needs to manually adjust the angles and positions of the three infrared range sensors 301, 302, 303 to align with the left shoulder, neck and right shoulder of the user, respectively. In some embodiments, the alignment with the neck, left shoulder, and right shoulder do not have to be very precise, for example the infrared range sensors are substantially aligned with the center positions of these body parts. For example, the angles and positions of the three infrared range sensors 301, 302, 303 can be manually adjusted to align with the center of a scapular region of the left shoulder, the fourth cervical vertebra of the posterior neck, and the center of a scapular region of the right shoulder of the user in a standard sitting posture. Depending on the height of the desk and the distance between the desk and the seat, the standard sitting posture is a sitting posture of the user sitting on the seat in a regular or strict sitting posture standard, such that the positions of the neck and the shoulder portions in the standard sitting posture are determined. Upon the angle and position being set, the positions of the three infrared range sensors 301, 302, and 303 are locked, and data (measured) in this situation is stored in the central control system 32 through a signal transmission line.

The infrared range sensors use an infrared signal for measuring distances. When the user sits on the seat, infrared signals of a specific frequency emitted by infrared signal emitting diodes of the infrared range sensors reach the neck and both shoulder positions of the user, and then are reflected back to infrared signal receiving diodes of the infrared range sensors, and distances to the corresponding positions are obtained through data calculation and processing.

A signal transmission line 34 used by the sitting posture detection device 3 is connected to the central control system 32 under the seat base in the hollow interior of the carrier rod support portion 313 along the seat back, as shown in FIGS. 2 and 3.

Figure 4:
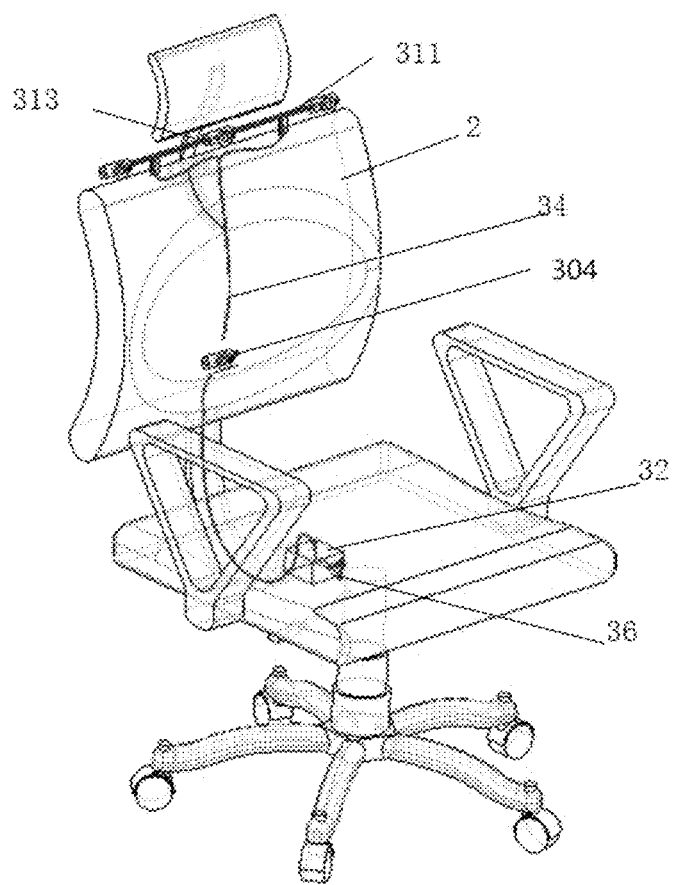
FIG. 4 shows a signal transmission line, a central control system, and a power source of the distance sensor device in accordance with an embodiment of the present disclosure.

FIG. 4 shows a signal transmission line 34, a central control system 32, and a power source 36 of the distance sensor device in accordance with an embodiment of the present disclosure. The signal transmission line 34 passes, from the infrared range sensors, through the carrier rod 311 and the carrier rod support portion 313, to the seat back of the seat frame 2 and then to the central control system 32 under the seat base 1. In addition, a distance sensor 304 corresponding to the waist is also shown in FIG. 4. The distance sensor 304 can measure a distance from the seat frame 2 to the waist of the user. The central control system 32 can determine whether the user's sitting posture is correct based on the data sensed by the distance sensors 301, 302, 303, and 304.

Figure 5:
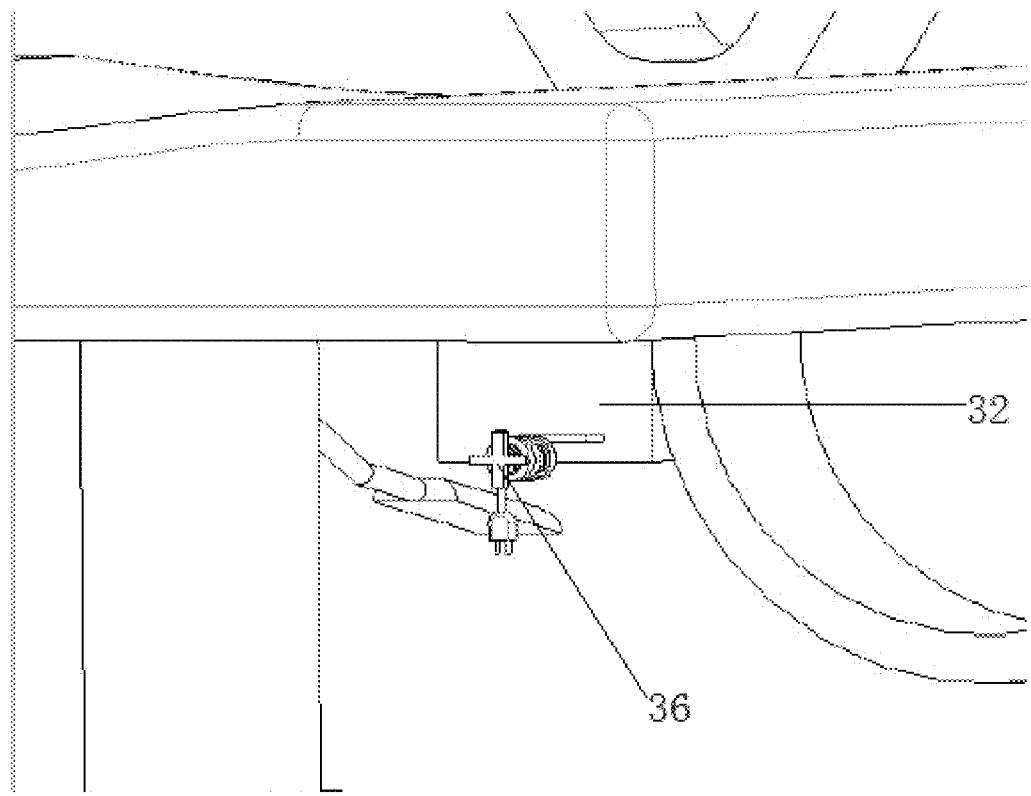
FIG. 5 is a schematic view showing the central control system and the power supply under the seat base of FIG. 1.

FIG. 5 is a schematic view showing the central control system 32 and the power supply 36 under the seat base 1 of FIG. 1. The power supply 36 may be a battery, and can be charged by connecting with a power cord when not in use. In some embodiments in accordance with the present disclosure, it is also possible to directly supply power through a power line without providing a battery.

Figure 6:
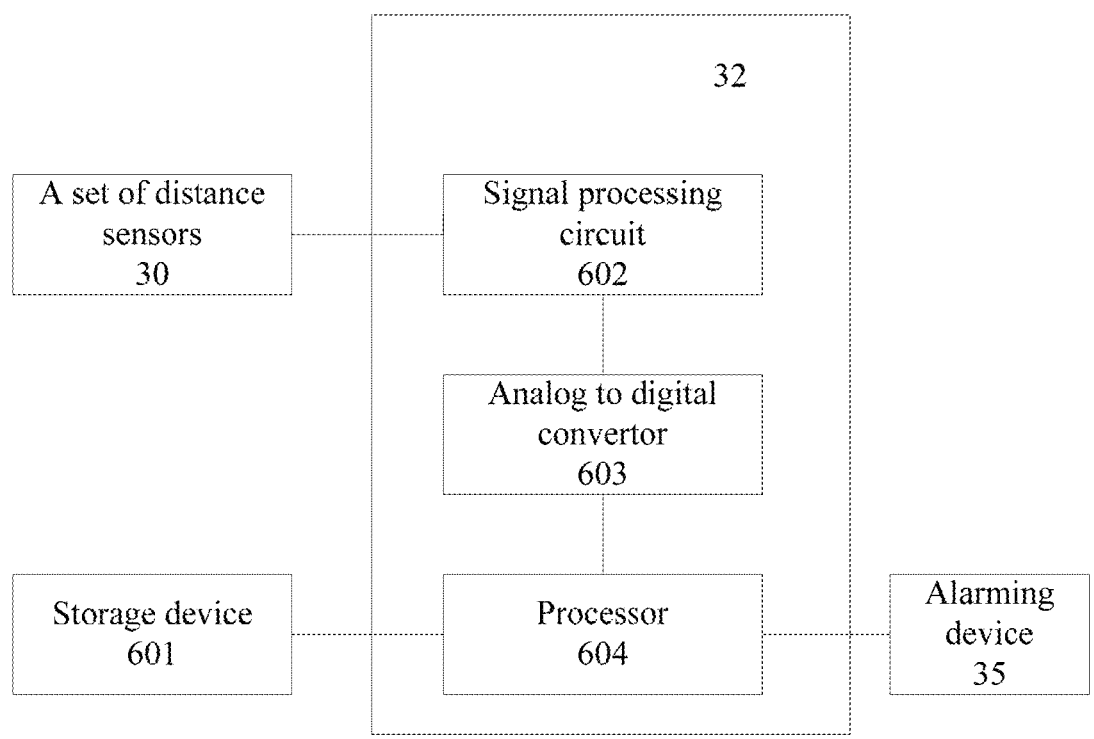
FIG. 6 is a block diagram of the central control system of the sitting posture detection device of FIG. 2.

FIG. 6 is a block diagram of some components of the sitting posture detection device 3. According to an embodiment of the present disclosure, the process of detecting sitting posture with infrared range sensors is as follows. After the power source 36 is turned on, a user sits on the seat, and the infrared range sensors are activated; through rotating the rotation shaft 312 of each of the infrared range sensors located at three different positions, horizontally shifting the infrared range sensors along the carrier rod 311, and sliding the carrier rod 311 along the carrier rod supporting portion 313, three infrared range sensors 301, 302, 303 are aligned with the user's left shoulder, neck and right shoulder respectively, and then the distance sensors 301, 302, 303, the carrier rod 311 and the carrier rod support portion 313 are locked. These initial standard positions are positions (standard distances) identified by the distance sensors when the user is in a correct sitting posture (standard sitting posture), and distance signals detected by the distance sensors passing through a signal processing circuit 602 are collected by an analog-to-digital converter 603 to the central control system 32 of the processor 604 (e.g., a chip microcomputer). In addition, storage processing can also be performed to store data in a storage device 601. This sensing process for distance detection can be repeated in real time (or periodically), detected in real time (or periodically). At the same time, the processor 604 of the central control system 32 continuously compares the detected distance data with an initial standard distance. If the difference between the detected distance data and the standard distance is within a certain tolerance range (for example, a predetermined threshold), the central control system 32 does not issue a warning signal. If the difference between the detected distance and the standard distance exceeds the preset tolerance range, a deviation from the correct sitting posture is determined and the user's sitting posture is incorrect. The processor 604 (e.g., a chip microcomputer) of the central control system 32 issues alarm information to the alarming device 35, by which the user sitting on the seat is warned to adjust the sitting posture until it is correct. The alarming device 35 can also be turned off if the user does not want to be disturbed by the alarm information.

Figure 7:
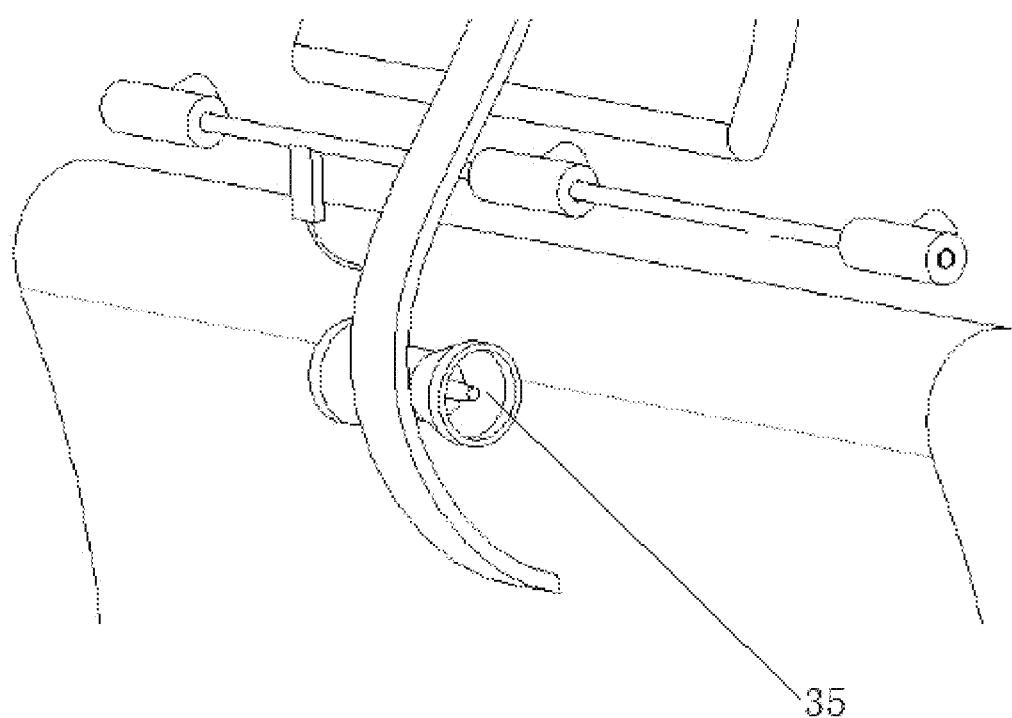
FIG. 7 shows a schematic view of an alarming device mounted behind the seat frame of the seat of FIG. 1.

FIG. 7 shows a schematic view of the alarming device 35 mounted behind the seat frame 2 of the seat of FIG. 1. The alarming device 35 may be a speaker, and a voice or music prompt signal can be selected as a voice setting of the speaker according to personal preference. Further, the alarming device 35 may also be, for example, a vibrator that can warn the user by generating vibration. In addition, multiple alarming devices can also be provided to facilitate the user to perform operations as needed.

It shall be noted that: the above embodiments are merely illustration of the technical solution of this disclosure, but are not limitation thereof. Although this disclosure has been described in detail with reference to the above embodiment, those ordinary skilled in the art shall understand: the technical solutions recited in the various embodiments described above may be modified or some technical features thereof may be substituted equivalently, such modifications or substitutions do not deviate the nature of the technique from the spirit and scope of the technique embodied in the embodiments according to this disclosure.

What is claimed is:

1. A seat, comprising:
   a seat base;
   a seat frame; and
   a sitting posture detection device configured to alert a user when a sitting posture of the user sitting on the seat deviates from a standard sitting posture,
   wherein the sitting posture detection device includes:
      one or more distance sensors configured to measure a distance from the seat frame to one or more body parts of the user;
      a processor configured to determine, according to the distance detected by the one or more distance sensors, whether the sitting posture of the user deviates from the standard sitting posture, and issue an alarm information if the sitting posture of the user deviates from the standard sitting posture; and
      a first support portion and a second support portion, a position of the first support portion corresponds to a position of a neck of the user in the standard sitting posture, a position of the second support portion corresponds to a position of a shoulder of the user in the standard sitting posture, and the one or more distance sensors are respectively disposed on the first support portion and the second support portion.

2. The seat according to claim 1, wherein the one or more body parts comprises a neck, a left shoulder, a right shoulder and a waist.

3. The seat according to claim 1, wherein the one or more distance sensors are infrared range sensors or laser sensors.

4. The seat according to claim 1, wherein the sitting posture detection device further comprises a carrier rod, the first support portion and the second support portion are mounted on the carrier rod, so that the one or more distance sensors can be rotated about the carrier rod to adjust angles of the one or more distance sensors and can be moved along the carrier rod.

5. The seat according to claim 4, wherein the sitting posture detection device further comprises a carrier rod support portion fixedly coupled to the seat frame, the carrier rod being configured to be slidable on the carrier rod support portion to adjust a height of the one or more distance sensors.

6. The seat according to claim 1, wherein the processor is configured to compare the distance measured by the one or more distance sensors to a standard distance which is measured by the one or more distance sensors when the user is in the standard sitting posture.

7. The seat according to claim 6, wherein when a difference between the distance measured by the one or more distance sensors and the standard distance is greater than a predetermined threshold, the processor issues the alarm information.

8. The seat according to claim 1, wherein the sitting posture detection device comprises an alarming device.

9. The seat according to claim 8, wherein the alarming device comprises a speaker and a vibrator.

10. The seat according to claim 6, wherein the sitting posture detection device comprises a storage device for storing the standard distance.

11. A method of detecting a sitting posture of a user sitting on the seat of claim 1, comprising:
    measuring the distance from the seat frame to the one or more body parts of the user;
    determining whether the sitting posture of the user deviates from the standard sitting posture according to the distance; and
    issuing the alarm information if the sitting posture of the user deviates from the standard sitting posture.

12. The method according to claim 11, wherein the one or more body parts comprises a neck, a left shoulder, a right shoulder and a waist.

13. The method according to claim 11, wherein determining whether the sitting posture of the user deviates from a standard sitting posture according to the distance comprises:
    comparing the distance to a standard distance which is measured when the user is in the standard sitting posture; and if a difference between the distance and the standard distance is greater than a predetermined threshold, determining that the sitting posture of the user deviates from the standard sitting posture.

\* \* \* \* \*